(12) United States Patent
Chichereau et al.

(10) Patent No.: US 6,292,536 B1
(45) Date of Patent: Sep. 18, 2001

US006292536B1

(54) METHOD OF ADJUSTMENT OF CONFIGURATION IN DIGITAL RADIOLOGY

(75) Inventors: Claire Chichereau, Paris; Agnes Le Roux, Versailles, both of (FR)

(73) Assignee: GE Medical Systems SA, Buc (FR)

( * ) Notice: Subject to any disclaimer, the term of this patent is extended or adjusted under 35 U.S.C. 154(b) by 0 days.

(21) Appl. No.: 09/450,494

(22) Filed: Nov. 29, 1999

(30) Foreign Application Priority Data

Nov. 27, 1998 (FR) ................................... 98 14979

(51) Int. Cl.⁷ ........................................ H05G 1/42
(52) U.S. Cl. .............................. 378/108; 378/37
(58) Field of Search ................ 378/108, 37, 62

(56) References Cited

FOREIGN PATENT DOCUMENTS

| 0402244 | 12/1990 | (EP) . |
| 0465360 | 8/1992 | (EP) . |
| 1004875 A2 | * 11/1999 | (EP) . |
| 1005258 A1 | * 11/1999 | (EP) . |
| 87/1555 | 3/1987 | (WO) . |

* cited by examiner

Primary Examiner—David V. Bruce
(74) Attorney, Agent, or Firm—Jay L. Chaskin

(57) ABSTRACT

The method consists of forming a preexposure image and deriving from it a mean preexposure detector signal level and converting it into a preexposure dose level, determining the equivalent radiologic thickness, estimating a composition of width examined and establishing a configuration of exposure and an exposure mA.s.

11 Claims, No Drawings

METHOD OF ADJUSTMENT OF CONFIGURATION IN DIGITAL RADIOLOGY

BACKGROUND OF THE INVENTION

The present invention relates to a method of adjustment of the parameters of exposure in digital radiology, and in particular in digital mammography.

Conventionally, in radiology, the parameters of exposure such as focal track selected (in the case of a device with double focal track), filter used, voltage applied to the tube (kV), presence or absence of grid, enlargement of contact and product of anodic current by duration of exposure (mA.s), constituting what is called the configuration, are initially determined from a selection of the user for the parameters of presence or absence of grid and enlargement or contact, and from a table of automatic optimization of parameters (AOP), as a function of the selections of the user, for the parameters kV, focal track, filter and mA.s. The organ part examined is then subjected to a preexposure with a low mA.s value to determine the characteristics of the organ part examined, in particular the equivalent radiologic thickness, and the parameters of exposure are then adjusted from these characteristics.

More precisely, at the time of preexposure an automatic exposure control (AEC) cell is used and the equivalent radiologic thickness is determined from the signal of the AEC cell. In order to obtain a good estimate of the equivalent radiologic thickness, 60 different parameters must be determined by means of the AEC calibration cell. An estimate of the composition of the organ part examined and an adjustment of the parameters of exposure (configuration) is then made with an initial estimate of mA.s.

During an exposure of the organ part examined with the previously determined configuration, the AEC cell continuously updates the mA.s value.

For further details concerning the method described above, reference is made to documents EP-0,402,244 and EP-0,465,360.

The method of adjustment of the configuration described above has the disadvantage of necessitating a specific calibration device, namely the AEC cell, and of requiring the determination of a large number of parameters.

BRIEF SUMMARY OF THE INVENTION

An embodiment of the present invention is a method of adjustment of the configuration, in digital radiology, which does not necessitate the use of a specific calibration cell and requires only a small number of parameters.

An embodiment of the present invention is a method of adjustment of the configuration necessitating a single image for each configuration and which uses the signals of the detector directly to effect adjustment of the exposure configuration.

DETAILED DESCRIPTION OF THE INVENTION

In an embodiment of the invention, the method of adjustment of the configuration, in digital radiology, comprises the steps of:

a) forming on an image receiver of a digital detector a preexposure image of an examined organ part with a selected configuration and a mA.s pre of low value (generally of the order of 1 to 4);

b) selecting a zone of interest in the preexposure image and extracting from it a mean preexposure signal level Signal_level_pre;

c) converting the mean preexposure signal level into a preexposure dose level IR_dose_pre by means of the relation:

$$\mathrm{IR\_dos\_pre} = \mathrm{IR\_dos\_ref} \cdot \frac{\mathrm{Signal\_level\_pre}}{\mathrm{Signal\_level\_ref}} \cdot \frac{\mathrm{IR\_gain\_ref}}{\mathrm{IR\_gain\_pre}} \quad (I)$$

wherein IR_dose_ref, Signal_level_ref and IR_gain_ref are, respectively, the dose, the mean signal level and the gain obtained in the course of a previous step of calibration of the detector, and Signal_level_pre and IR_gain_pre are, respectively, the mean preexposure signal level and the gain of the detector in the course of the preexposure step;

d) determining an equivalent radiologic thickness by means of the relation:

$$\mathrm{rad\_thickness} = \quad (II)$$
$$A + F_O(\mathrm{kV}) + F_1(\mathrm{kV})\log\left[\frac{\mathrm{IR\_dos\_pre}}{\mathrm{mA \cdot s\ pre}}\right] + F_2(\mathrm{kV})\log\left[\frac{\mathrm{IR\_dos\_pre}}{\mathrm{mA \cdot s\ pre}}\right]^2$$

wherein rad thickness is the equivalent radiologic thickness, IRdose ref is the preexposure dose determined in step c) and mA.s pre is the preexposure value of mA.s;

$$F_i(\mathrm{kV}) = \sum_{j=0 \& 2} A_i^j \mathrm{kV}^j \quad i = 0\ \mathrm{to}\ 2\ i = 0\ \mathrm{to}\ 2, \quad (III)$$

The coefficients $A_i^j$ characterizing the selected configuration and being established once and for all and the coefficient A corresponding to the configuration being established in the course of the step of calibration of the detector; and e) estimating a composition of the organ part examined and establishing an exposure configuration by calculating the mA.s of exposure by means of the relation:

$$\mathrm{mA} \cdot \mathrm{s}_{\exp} = \mathrm{mA} \cdot \mathrm{s}_{ref} \cdot \frac{\mathrm{IR\_dos\_target} \cdot scf_{pre}}{\mathrm{IR\_dos\_ref} \cdot scf_{pre}} \quad (IV)$$

wherein IR dose target is a dose selected by the operator, scfpre and scfexp are conversion factors dependent upon the configuration during preexposure and exposure, respectively.

The conversion factors scf are calculated from the relation:

$$scf = \exp[(G_0(\mathrm{kV}) + G_1(\mathrm{kV})\mathrm{rad\_thickness} + G_2(\mathrm{kV})(\mathrm{rad\_thickness})^2]$$

wherein rad thickness is the radiologic thickness and the coefficients Gi(kV) are established once and for all from a model according to the relation:

$$G_1(\mathrm{kV}) = B_i^0 + B_i^1 \mathrm{kV} + B_i^2\ \mathrm{kV}^2$$

the coefficients $B_i^j$ being parameters characterizing a configuration. Nine Bji coefficients are sufficient to determine the scf conversion factors.

As results from relations (II) and (III), only 9 parameters are used for characterizing a configuration.

The calibration step making it possible to obtain the values of IR dose ref, Signal level ref and of the coefficient A will now be described.

To determine IR dose ref, a dosimeter is placed on the image receiver of the detector and a filter of known thickness (for example a 5-cm lucite plate) is arranged before the receiver and the dosimeter to approach normal operating conditions as closely as possible, and the detector is irradiated with a given configuration. The dosimeter makes it possible to obtain the measurement of IR dose ref.

The dosimeter is removed and the quantity Signal level ref is measured directly on the image receiver of the detector, at the location of the dosimeter.

To determine the coefficients A, the detector is irradiated, always through the lucite plate and without dosimeter, for all possible configurations of the following parameters of exposure: focal track, filter, width of focus and presence or absence of grid, and the mean signal level of the detector is measured on the detector for each one of the configurations and is converted into IR dose cal by means of a relation similar to the relation (I). Then, the coefficients A are determined for all configurations by means of the relation:

$$A = F_O(kV) + F_1(kV)\log\left[\frac{IR\_dos\_cal}{mA \cdot s_{cal}}\right] + F_2(kV)\log\left[\frac{IR\_dos\_cal}{mA \cdot s_{cal}}\right]^2 - \text{lucite\_thickness} \quad (V)$$

wherein mA.scal corresponds to the mA.s used during calibration, lucite thickness is the thickness of the filter interposed at the time of calibration and the functions Fi(kV) are as previously defined.

A table of coefficients A, which are selected and used in the course of the method of the invention as a function of the configuration, is thus obtained.

Estimation of the composition of the organ part examined is conventional. Thus, in mammography, conventionally the composition of a breast examined is estimated from the relation between the mechanical thickness and the radiologic thickness (an average case is a breast consisting 50% of glandular fibers and 50% of adipose tissues).

Various modifications in structure and/or function and/or steps may be made by one skilled in the art to the disclosed embodiments without departing from the scope and extent of the invention.

What is claimed is:

1. A method of configuration control, in digital radiology, comprising the steps of:

a) forming on an image receiver of a digital detector a preexposure image of an examined organ part with a selected configuration and a mA.s pre of low value;

b) selecting a zone of interest in the preexposure image and extracting from it a mean preexposure signal level Signal_level_pre;

c) converting the mean preexposure signal level into a preexposure dose level IR dose pre by means of the relation:

$$IR\_dos\_pre = IR\_dos\_ref \cdot \frac{Signal\_level\_pre}{Signal\_level\_ref} \cdot \frac{IR\_gain\_ref}{IR\_gain\_pre} \quad (I)$$

wherein IR dose ref, Signal level ref and IR gain ref are, respectively, the dose, the mean signal level and the gain obtained in the course of a previous step of calibration of the detector, and Signal level pre and IR gain pre are, respectively, the mean preexposure signal level and the gain of the detector in the course of the preexposure step;

d) determining an equivalent radiologic thickness by means of the relation:

$$\text{rad\_thickness} = \quad (II)$$
    $$A + F_O(kV) + F_1(kV)\log\left[\frac{IR\_dos\_pre}{mA \cdot s\ pre}\right] + F_2(kV)\log\left[\frac{IR\_dos\_pre}{mA \cdot s\ pre}\right]^2$$

wherein rad thickness is the equivalent radiologic thickness, IR dose ref is the preexposure dose determined in step c) and InA.s pre is the preexposure value of mA.s;

$$F_i(kV) = \sum_{j=0\delta 2} A_i^j kV^j \quad i = 0 \text{ to } 2 \quad i = 0 \text{ to } 2, \quad (III)$$

the coefficients Aji characterizing the selected configuration and being established once and for all and the coefficient A corresponding to the configuration being established in the course of the step of calibration of the detector; and e) estimating a composition of the organ part examined and establishing an exposure configuration by calculating the mA.s of exposure by means of the relation:

$$mA \cdot s_{exp} = mA \cdot s_{ref} \cdot \frac{IR\_dos\_target \cdot scf_{pre}}{IR\_dos\_ref \cdot scf_{pre}} \quad (IV)$$

wherein IR dose target is a dose selected by the operator, scfpre and scfexp are conversion factors dependent upon the configuration during preexposure and exposure, respectively.

2. The method according to claim 1, wherein the RI dose ref is determined during the calibration step by means of a dosimeter placed on the image receiver of the detector.

3. The method according to claim 2, wherein the Signal level ref is determined directly on the image receiver after removal of the dosimeter and at the location of the dosimeter.

4. The method according claim 1, wherein during calibration a filter of given thickness simulating standard conditions of use is arranged before the image receiver.

5. The method according to claim 2, wherein during calibration a filter of given thickness simulating standard conditions of use is arranged before the image receiver.

6. The method according to claim 3, wherein during calibration a filter of given thickness simulating standard conditions of use is arranged before the image receiver.

7. The method according to claim 4, wherein the coefficient A corresponding to the configuration is selected from among a table of coefficients A established in the calibration step.

8. The method according to claim 5, wherein the coefficient A corresponding to the configuration is selected from among a table of coefficients A established in the calibration step.

9. The method according to claim 6, wherein the coefficient A corresponding to the configuration is selected from among a table of coefficients A established in the calibration step.

10. The method according to claim 5, wherein the table of coefficients A is established by determining, for all possible configurations, parameters of exposure, track, filter, size of focus, presence or absence of grid, the quantity IR dose cal received by the receiver and by means of the relation:

$$A = F_O(kV) + F_i(kV)\log\left[\frac{IR\_dos\_cal}{mA \cdot s_{cal}}\right] + F_2(kV)\log\left[\frac{IR\_dos\_cal}{mA \cdot s_{cal}}\right]^2 - lucite\_thickness \quad (V)$$

where ma.Scal is the mA.s used in calibration and lucite thickness is the thickness of the filter interposed before the image receiver.

11. The method according to claim 1, wherein the conversion factors scf are determined for each configuration by means of the relation:

$$scf = \exp[(G_0(kV) + G_1(kV)rad\_thickness + G_2(kV)(rad\_thickness)^2)]$$

wherein rad thickness is the equivalent radiologic thickness and Gi(kV) are coefficients, dependent upon the configuration, established once and for all from a model.

* * * * *